United States Patent [19]

Okabe et al.

[11] Patent Number: 4,930,861
[45] Date of Patent: Jun. 5, 1990

[54] TELEVISION CAMERA FOR ENDOSCOPES

[75] Inventors: Minoru Okabe, Kanagawa; Akira Kikuchi, Tokyo, both of Japan

[73] Assignee: Olympus Optical Co., Ltd., Tokyo, Japan

[21] Appl. No.: 269,610

[22] Filed: Nov. 10, 1988

[30] Foreign Application Priority Data

Nov. 12, 1987 [JP] Japan .................................. 62-286293
Dec. 9, 1987 [JP] Japan .................................. 62-309683

[51] Int. Cl.⁵ ............................................ G02B 23/26
[52] U.S. Cl. ............................. 350/96.25; 350/96.26; 350/162.12; 350/447; 350/502; 358/901
[58] Field of Search ............. 350/96.25, 96.26, 162.12, 350/447, 448, 502, 530

[56] References Cited

U.S. PATENT DOCUMENTS 4,676,592 6/1987 Nishioka et al. ................. 350/96.25
4,676,593 6/1987 Adachi et al. .................... 350/96.26
4,720,637 1/1988 Clark ................................... 250/578

Primary Examiner—John D. Lee
Attorney, Agent, or Firm—Cushman, Darby & Cushman

[57] ABSTRACT

A TV camera for endoscopes comprising an image guide fiber bundle, an imaging optical system and an image sensor, used for focusing an image formed on the end surface of the image guide fiber bundle onto the imaging surface of the image sensor by the imaging optical system, and so adapted as to adjust diameter of the circle of confusion on the optimum image plane of the imaging optical system or the position of an image formed by the imaging optical system.

13 Claims, 17 Drawing Sheets

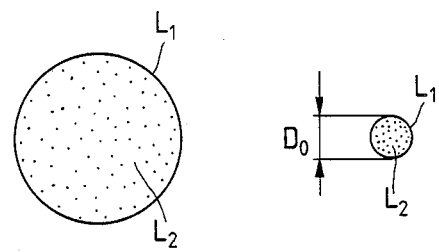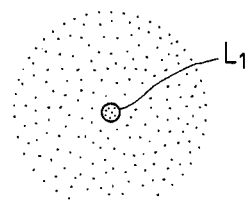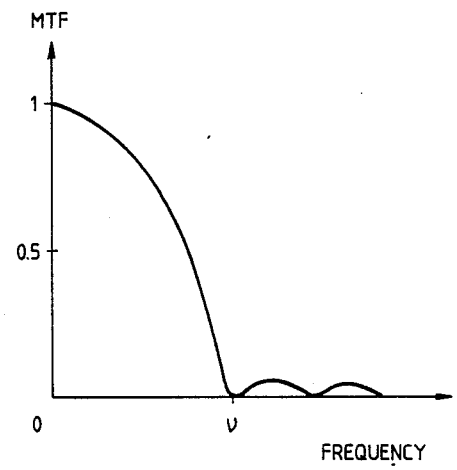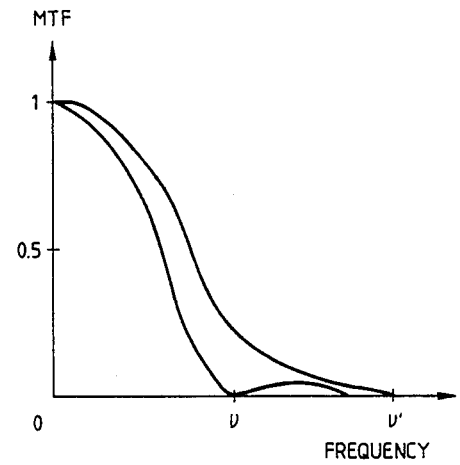

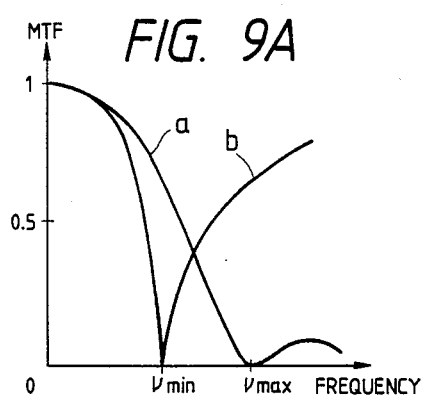
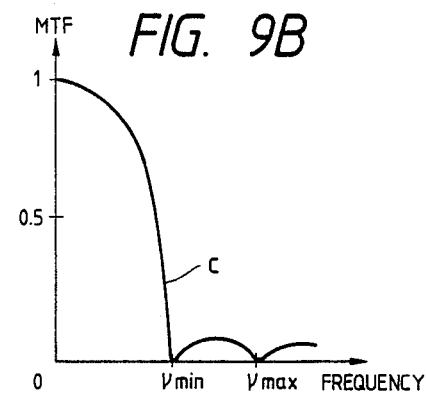
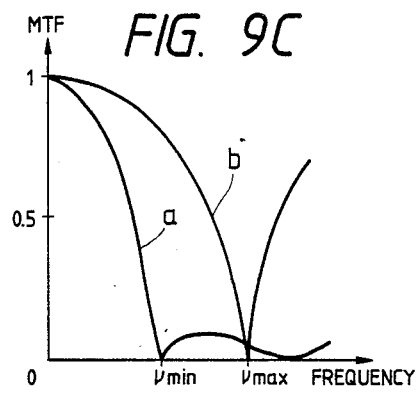
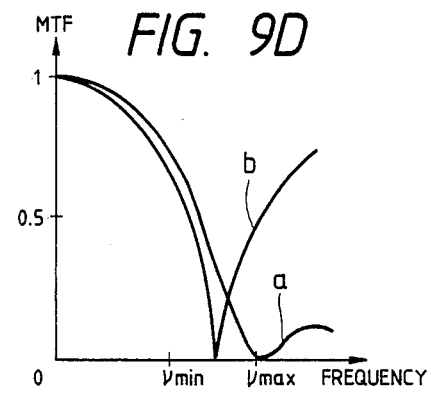
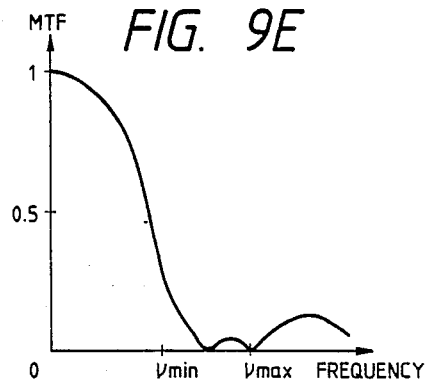

TELEVISION CAMERA FOR ENDOSCOPES

BACKGROUND OF THE INVENTION

1. Field of the invention:

The present invention relates to a television camera (hereinafter TV camera) for endoscopes.

2. Description of the prior art:

In the recent years, it is increasingly practiced to observe narrow locations such as interiors of coelomata in the form of images on TV screens by attaching cameras to eyepieces of fiberscopes. FIG. 1 shows a schematic sectional view illustrating a fiberscope to which a TV camera is attached. As shown in this drawing, a fiberscope 10 comprises an objective lens 1, an image guide fiber bundle 2 and an eyepiece lens 3, and an image of an object is generally observed through the eyepiece lens 3. A TV camera 20 attached to the eyepiece 3 of the fiberscope 10 comprises an imaging lens 5 and a solid-state image sensor 6, and an image of an object formed on the exit end surface of the image guide fiber bundle 2 is focused by the eyepiece lens 3 and the imaging lens 5 again onto the light receiving surface of the solid-state image sensor 6 for enabling observation of the image through the TV camera.

The exit end surface of the image guide fiber bundle has a mesh structure wherein a multiple number of optical fibers are regularly arranged. When an image of the end surface is projected onto the solid-state image sensor 6, the mesh structure is reproduced and, since the period of the mesh structure is close to the period of the arrangement of the picture elements in the image sensor or that of the arrangement of the filter elements of the color encoding filter array used in combination with the image sensor as occasion demands, false signals called "moiré" (or aliasing) are produced in the image formed on the TV screen. These TV cameras produce the false signals far more remarkably than the general TV cameras.

In order to eliminate the moiré it is general to use optical low pass filters. U.S. Pat. No. 4,100,570, for example, uses an optical low pass filter consisting of a birefringent plate such as quartz arranged in the imaging optical path of a TV image pick up system for eliminating the moiré Further, U.S. Pat. No. 4,417,272 adopts an optical low pass filter consisting of a prism.

A TV camera applying these techniques is disclosed by U.S. Pat. No. 4,676,593. This TV camera is so adapted as to eliminate the moiré by arranging an optical low pass filter such as a quartz plate or a phase filter with an adapter lens which is disposed in the eyepiece optical system or between the TV camera and the eyepiece lens at the stage to attach the TV camera to the eyepiece of an endoscope. However, it is impossible to completely eliminate the moiré in a TV camera for endoscopes, separately from the general TV cameras, simply by arranging an optical low pass filter as in the case of the above-mentioned example. This is because thickness of image guide fiber bundles is various and thickness of optical fibers proper composing the optical fiber bundles is also various for individual endoscopes used, whereby periods of mesh structures in the images formed on the light receiving surfaces of image sensors are different even for the same TV camera. When the above-mentioned periods are different, the moiré is produced in various manners and cannot be eliminated sufficiently with a single optical low pass filter.

Further, Japanese Unexamined Published Utility Model Appln. No. 12145/61 discloses a TV camera so adapted as to use selectively, in accordance with objects to be photographed, a plural number of optical low pass filters which are prepared in advance. However, this example is undesirable since it inevitably enlarges the TV camera and complicates the composition thereof.

As another means to eliminate the moiré U.S. Pat. No. 4,720,637 discloses a means to impart a relatively large spherical aberration to the imaging lens itself and limit spatial frequency spectrum of an image formed on the light receiving surface of the image sensor to the Nyquist frequency of the image sensor by the spherical aberration. Though this correcting means is applicable to the ordinary TV cameras, it cannot sufficiently eliminate the moiré which is very remarkable in the TV camera for endoscopes.

SUMMARY OF THE INVENTION

A primary object of the present invention is to provide a TV camera usable in combination with a plural number of fiberscopes different from one another and so adapted as to prevent the moiré from being produced when combined with any one of the fiberscopes. The TV camera for endoscopes according to the present invention comprises an imaging lens and a solid-state image sensor, and is to be used in a condition attached to an eyepiece of a fiberscope.

In order to accomplish the object of the present invention, the TV camera for endoscopes according to the present invention is so adapted as to eliminate the moiré by minimizing value of the MTF (modulation transfer function) at a spatial frequency which is determined by arrangement of fibers on the exit end surface of an image guide fiber bundle of a fiberscope and/or the spatial frequency which is determined by arrangement of picture elements in a solid-state image sensor or period of a color encoding filter array used in combination therewith.

In order to minimize value of the MTF, the TV camera for endoscopes according to the present invention comprises an imaging lens having aberration to impart blurring of a predetermined degree to an image of an object and an optical low pass filter arranged in the optical path of the camera at a location before the solid-state image sensor. Further, in the TV camera for endoscopes according to the present invention the solid-state image sensor is arranged at a location a little deviated from the out-of-focus position of an image of an object formed by the imaging lens and the optical low pass filter is arranged in the optical path of the camera. In other words, the distance between the imaging lens and the solid-state image sensor is determined so as to set the image formed by the imaging lens on the solid-state image sensor in out-of-focus condition.

BRIEF DESCRIPTION OF THE DRAWINGS

FIGS. 4A–4C show diagrams illustrating conditions of said light bundle in the direction perpendicular to the optical axis;

FIG. 5 shows a graph illustrating the MTF in the vicinity of the image plane of said imaging optical system;

FIG. 6 shows graphs illustrating the MTF zeroed at high frequencies;

FIG. 9A through FIG. 9E show graphs illustrating relations of the MTF versus cut-off frequencies of optical fibers and optical low pass filters respectively;

DETAILED DESCRIPTION OF THE PREFERRED EMBODIMENTS

Figure 1:
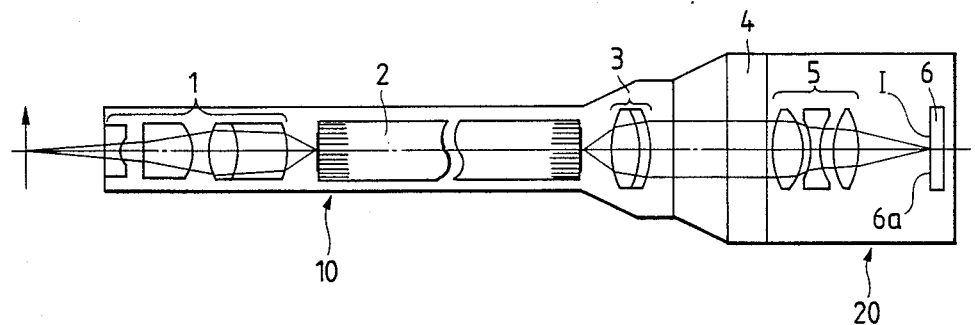
FIG. 1 shows a schematic sectional view illustrating the conventional TV camera for endoscopes in a condition attached to a fiberscope.
Figure 2:
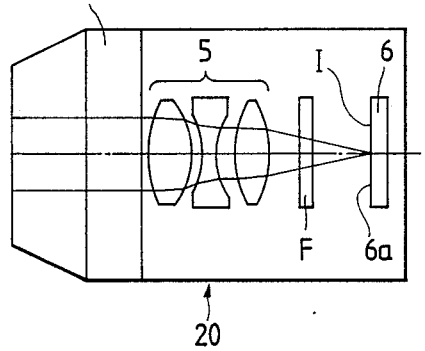
FIG. 2 shows a sectional view illustrating fundamental composition of the TV camera for endoscopes according to the present invention.

FIG. 2 shows a sectional view schematically illustrating the Embodiment 1 of the TV camera for endoscopes according to the present invention. As shown in this drawing, the TV camera 20 for endoscopes according to the present invention has a rotating member 4, and comprises an imaging lens 5, an optical low pass filter F and a solid-state image sensor 6. The TV camera for endoscopes according to the present invention is used, like the conventional example, in a condition attached to various types of fiberscopes. The TV camera for endoscopes according to the present invention can be rotated around the optical axis by using the rotating member 4 in the condition where a fiberscope is attached to the TV camera.

The imaging lens 5 of the TV camera 20 according to the present invention has the characteristic described below. Speaking concretely, the imaging lens 5 used in the TV camera 20 according to the present invention has spherical aberration of the definite degree so as to satisfy the following condition:

$$D_0 \geq 0.6/\nu$$

wherein the reference symbol $\nu$ represents the spatial frequency corresponding to the Nyquist frequency of the solid-state image sensor 6 or the spatial frequency expressing a period of optical fiber arrangement in an image of an image fiber bundle projected to the solid-state image sensor 6, and the reference symbol $D_0$ designates the diameter of a circle of confusion on the optimum image plane of an image formed by the imaging lens 5 (the diameter of the minimum circle of confusion).

The fiberscope 10 and the TV camera 20 are assembled in such a manner that the TV camera 20 is rotatable with the rotating member 4 relative to the fiberscope 10. The rays emitted from the image fiber bundle 2 pass through the eyepiece lens 3 and are focused by the imaging lens 5 on the image sensor 6. Further, by rotating the TV camera with the rotating member 4, the angle formed between the image fiber bundle and the arrangement direction of the picture elements in the image sensor is adjusted.

Figure 3:
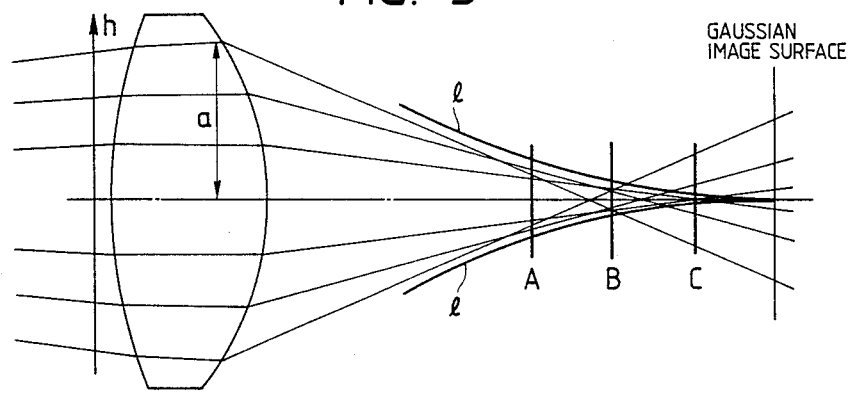
FIG. 3 shows a sectional view illustrating converged condition of a light bundle when spherical aberration is produced in the imaging optical system used by the present invention.

When spherical aberration is produced by the imaging lens, the paraxial ray emitted from the eyepiece of the fiberscope 10 is focused on the image sensor as shown in FIG. 3. When three points of A, B and C are considered on the optical axis in this case, the diameter $D_0$ of the minimum circle of confusion is obtained at the point B. The point B is located at a position where a circular line $L_1$ which is an intersection between the imaging plane of the image sensor and ray 1 as shown in FIG. 4B, is coincident with the size of an image $L_2$ on a circular plate on which another ray intersects with the imaging plane, and is therefore the optimum image plane when the imaging lens produces aberration. Further, the point A is an image plane deviated from the point B toward the object side, whereas the point C is an image plane deviated from the point B in the direction opposite to the point A. At these points A and C, circles of confusion have diameters larger than the diameter $D_0$ of the circle of confusion at the point B as shown in FIG. 4A and FIG. 4C respectively.

In order to prevent the moiré from being produced in a TV camera used in combination with a fiberscope using an image guide fiber bundle as described above, it is sufficient to zero image contrast at the spatial frequency when an image is formed on the image sensor. In other words, it is sufficient for this purpose to design the imaging lens 6 so as to have a spatial frequency response shown in FIG. 5.

Let us here assume that an image transferred through an image guide fiber bundle is focused as an optimum image on the image sensor in the TV camera for endoscopes by using an image forming optical system composed of an eyepiece lens and imaging lens. At this time, the cut-off frequency at which the MTF determined by the diameter $D_0$ of the minimum circle of confusion is zeroed can be calculated by the following equation utilizing Fourier transformation:

$$\nu = 1.22/D_0$$

This equation can be transformed as follows:

$$D_0 = 1.22/\nu$$

That is to say, the diameter $D_0$ of the minimum circle of confusion for zeroing contrast can be calculated when the frequency depending on fiber diameter or the Nyquist frequency is determined.

In order to eliminate the moiré stripes completely, it is necessary to set the diameter $D_0$ of the minimum circle of confusion at the value calculated above. For actual observation, however, no hindrance is constituted when the diameter $D_0$ has a value about a half of the value calculated above. This is because contrast at the frequency $\nu$ can be lowered sufficiently by zeroing contrast at the frequency determined depending on a fiber diameter or at a frequency $\nu'$ higher than the Nyquist frequency $\nu$ as seen from FIG. 5. Accordingly, it is possible to eliminate the moiré to such a degree as not to hinder observation. Moreover, degradation of image quality can be limited to a low degree since contrast is high in the low frequency range. Taking this point into consideration, it is sufficient to select a value of $D_0$ that is within the range defined by the following condition (1):

$$D_0 \geq 0.6/\nu$$

Since spherical aberration $\Delta S'$ is proportional to square of height of the light incident on a lens, the following relation establishes:

$$\Delta S' \approx A_1 h^2$$

$A_1$ has a positive value in FIG. 2. For a ray having height $h=a$, the diameter $D_0$ is calculated as:

$$D_0 = \frac{1}{2}(A_1 a^3/f)$$

wherein the reference symbol $A_1 a^3/f$ represents a maximum value of spherical aberration. Hence, relation between the spherical aberration and the cut-off frequency $\nu$ is expressed as follows:

$$1.22/\nu = \frac{1}{2}(A_1 a^3/f)$$

On the basis of the fact described above, the condition (1) can be transformed as follows:

$$A_1 a^2/f > \frac{1}{2}/\nu a \quad (1')$$

As a concrete example of an imaging lens satisfying the condition (1'), it is conceivable to design a triplet type or Tesser type lens system having a stop arranged therebefore. That is to say, this lens system comprises a first lens component having positive refractive power, a second lens component having negative refractive power and a third lens component having positive refractive power. In order to produce spherical aberration in the negative direction in this type lens system, it is effective to design it so as to satisfy the following condition (2):

$$\Phi_2 + \Phi_3 > -0.5 \quad (2)$$

wherein the reference symbols $\Phi_2$ and $\Phi_3$ represent powers of the second and third surfaces respectively in the lens system. $\Phi_2$ and $\Phi_3$ are given as follows:

$$\Phi_2 = (1-n_1)/r_2, \quad \Phi_3 = (n_2-1)/r_3$$

wherein the reference symbols $r_1$ and $r_2$ represent radii of curvature on the second and third surfaces respectively, and the reference symbols $n_1$ and $n_2$ designate refractive indices of the first and second lens components respectively.

When the condition (2) is satisfied, $\Phi_2$ ($>0$) has strong power and spherical aberration is produced in the negative direction. Such a lens system will be described later as Examples 1, 2 and 6. In this case, it is more preferable to design the lens system so as to satisfy the condition defined below:

$$0 < -r_2/r_1 < 0.7$$

wherein the reference symbol $r_1$ represents radius of curvature on the first surface in the lens system.

Further, in order to produce spherical aberration in the positive direction in the triplet type lens system, it is desirable to design the lens system so as to satisfy the following conditions (3) and (4):

$$\Phi_2 + \Phi_3 < -0.55 \quad (3)$$

$$0.3 < -r_2/r_1 < 1 \quad (4)$$

When the condition (3) is satisfied, spherical aberration is produced in the positive direction since $\Phi_3$ ($<0$) has strong power and $\Phi_2$ ($>0$) has weak power. This lens system will be described as Examples 3, 4, 5, 7 and 8 of the imaging lens.

Degree of the spherical aberration to be produced in the triplet or Tesser type lens system having a stop arranged therebefore is largely dependent on refractive power of the meniscus-shaped air lens formed between the first lens component and the second lens component as well as shape of the first lens component.

If the above-mentioned condition (2) or the conditions (3) and (4) are not satisfied, the powers $\Phi_2$ and $\Phi_3$ of the second surface and the third surface will function to minimize degree of the spherical aberration to be produced. In such a case, since the diameter $D_0$ of the minimum circle of confusion on the optimum image plane is minimized, the image contrast (MFT) is enhanced at the cut-off frequency required for preventing the moiré to be produced, thereby allowing the moiré to be produced.

In the next place, when the imaging optical system is a single lens or an achromatic doublet, it is very effective for producing the spherical aberration remarkably in the negative direction to design the lens so as to satisfy the following condition (5):

$$|r_B/r_A| < 1 \quad (5)$$

If the condition (5) is not satisfied, degree of the spherical aberration to be produced will be minimized. Accordingly, the diameter $D_0$ of the minimum circle of confusion will be minimized at the optimum image plane and the image contrast (MTF) is not zeroed at the cut-off frequency required for preventing the moiré from being produced, thereby allowing the moiré to be produced.

Concrete examples of the imaging lens used in the TV camera according to the present invention are illustrated in FIG. 10 through FIG. 13 and have the following numerical data:

| Example 1 |
|---|
| $f = 1.000, F/4.818, IH = 0.115, OB = -19.0447$ |

| | | | |
|---|---|---|---|
| $r_1 = \infty$ (stop) | | | |
| | $d_1 = 0.0114$ | | |
| $r_2 = \infty$ | | | |
| | $d_2 = 0.0381$ | $n_1 = 1.51633$ | $\nu_1 = 64.15$ |
| $r_3 = \infty$ | | | |
| | $d_3 = 0.7542$ | | |
| $r_4 = 1.9888$ | | | |
| | $d_4 = 0.1425$ | $n_2 = 1.71300$ | $\nu_2 = 53.84$ |
| $r_5 = -0.5621$ | | | |
| | $d_5 = 0.0807$ | | |
| $r_6 = -0.5219$ | | | |
| | $d_6 = 0.0628$ | $n_3 = 1.64769$ | $\nu_3 = 33.80$ |
| $r_7 = 0.4323$ | | | |

-continued

| | | | |
|---|---|---|---|
| $r_8 = 0.8380$ | $d_7 = 0.1078$ | | |
| $r_9 = -0.6580$ | $d_8 = 0.1676$ | $n_4 = 1.69680$ | $\nu_4 = 55.52$ |
| $r_{10} = \infty$ | $d_9 = 0.1676$ | | |
| $r_{11} = \infty$ | $d_{10} = 0.0609$ | $n_5 = 1.51633$ | $\nu_5 = 64.15$ |
| $\phi_2 + \phi_3 = 0.02744$, $|r_2/r_1| = 0.28263$ | | | |

Example 2
f = 1.000, F/4.817, IH = 0.113, OB = −19.0512

| | | | |
|---|---|---|---|
| $r_1 = \infty$ (stop) | $d_1 = 0.0114$ | | |
| $r_2 = \infty$ | $d_2 = 0.0381$ | $n_1 = 1.51633$ | $\nu_1 = 64.15$ |
| $r_3 = \infty$ | $d_3 = 0.7544$ | | |
| $r_4 = 1.5769$ | $d_4 = 0.1425$ | $n_2 = 1.71300$ | $\nu_2 = 53.84$ |
| $r_5 = -0.6272$ | $d_5 = 0.0808$ | | |
| $r_6 = -0.4695$ | $d_6 = 0.0629$ | $n_3 = 1.64769$ | $\nu_3 = 33.80$ |
| $r_7 = 0.4695$ | $d_7 = 0.1078$ | | |
| $r_8 = 0.7161$ | $d_8 = 0.1677$ | $n_4 = 1.69680$ | $\nu_4 = 55.52$ |
| $r_9 = -0.7161$ | $d_9 = 0.1677$ | | |
| $r_{10} = \infty$ | $d_{10} = 0.0610$ | $n_5 = 1.51633$ | $\nu_5 = 64.15$ |
| $r_{11} = \infty$ | | | |
| $\phi_2 + \phi_3 = -0.24273$, $|r_2/r_1| = 0.39774$ | | | |

Example 3
f = 1.000, F/4.818, IH = 0.112, OB = −19.0592

| | | | |
|---|---|---|---|
| $r_1 = \infty$ (stop) | $d_1 = 0.0114$ | | |
| $r_2 = \infty$ | $d_2 = 0.0381$ | $n_1 = 1.51633$ | $\nu_1 = 64.15$ |
| $r_3 = \infty$ | $d_3 = 0.7547$ | | |
| $r_4 = 1.0138$ | $d_4 = 0.1426$ | $n_2 = 1.71300$ | $\nu_2 = 53.84$ |
| $r_5 = -0.7985$ | $d_5 = 0.0808$ | | |
| $r_6 = -0.4071$ | $d_6 = 0.0629$ | $n_3 = 1.64769$ | $\nu_3 = 33.80$ |
| $r_7 = 0.4830$ | $d_7 = 0.1079$ | | |
| $r_8 = 0.6815$ | $d_8 = 0.1677$ | $n_4 = 1.69680$ | $\nu_4 = 55.52$ |
| $r_9 = -0.6738$ | $d_9 = 0.1677$ | | |
| $r_{10} = \infty$ | $d_{10} = 0.0610$ | $n_5 = 1.51633$ | $\nu_5 = 64.15$ |
| $r_{11} = \infty$ | | | |
| $\phi_2 + \phi_3 = -0.69806$, $|r_2/r_1| = 0.78763$ | | | |

Example 4
f = 1.000, F/4.818, IH = 0.112, OB = −19.0658

| | | | |
|---|---|---|---|
| $r_1 = \infty$ (stop) | $d_1 = 0.0114$ | | |
| $r_2 = \infty$ | $d_2 = 0.0381$ | $n_1 = 1.51633$ | $\nu_1 = 64.15$ |
| $r_3 = \infty$ | $d_3 = 0.7550$ | | |
| $r_4 = 0.9396$ | $d_4 = 0.1426$ | $n_2 = 1.71300$ | $\nu_2 = 53.84$ |
| $r_5 = -0.7934$ | $d_5 = 0.0808$ | | |
| $r_6 = -0.3594$ | $d_6 = 0.0629$ | $n_3 = 1.64769$ | $\nu_3 = 33.80$ |
| $r_7 = 0.5172$ | $d_7 = 0.1079$ | | |
| $r_8 = 0.6908$ | $d_8 = 0.1678$ | $n_4 = 1.69680$ | $\nu_4 = 55.52$ |
| $r_9 = -0.6487$ | $d_9 = 0.1678$ | | |
| $r_{10} = \infty$ | $d_{10} = 0.0610$ | $n_5 = 1.51633$ | $\nu_5 = 64.15$ |
| $r_{11} = \infty$ | | | |
| $\phi_2 + \phi_3 = -0.90348$, $|r_2/r_1| = 0.84440$ | | | |

Example 5
f = 1.000, F/4.818, IH = 0.112, OB = −19.0643

| | | | |
|---|---|---|---|
| $r_1 = \infty$ (stop) | $d_1 = 0.0114$ | | |
| $r_2 = \infty$ | $d_2 = 0.0381$ | $n_1 = 1.51633$ | $\nu_1 = 64.15$ |
| $r_3 = \infty$ | $d_3 = 0.7549$ | | |
| $r_4 = 0.9206$ | $d_4 = 0.1426$ | $n_2 = 1.71300$ | $\nu_2 = 53.84$ |
| $r_5 = -0.8186$ | $d_5 = 0.0808$ | | |
| $r_6 = -0.3287$ | $d_6 = 0.0629$ | $n_3 = 1.64769$ | $\nu_3 = 33.80$ |
| $r_7 = 0.6457$ | $d_7 = 0.1079$ | | |
| $r_8 = 0.7287$ | $d_8 = 0.1678$ | $n_4 = 1.69680$ | $\nu_4 = 55.52$ |
| $r_9 = -0.6493$ | $d_9 = 0.1678$ | | |
| $r_{10} = \infty$ | $d_{10} = 0.0610$ | $n_5 = 1.51633$ | $\nu_5 = 64.15$ |
| $r_{11} = \infty$ | | | |
| $\phi_2 + \phi_3 = -1.09946$, $|r_2/r_1| = 0.88920$ | | | |

Example 6
f = 1.000, F/4.818, IH = 0.115, OB = −19.0453

| | | | |
|---|---|---|---|
| $r_1 = \infty$ (stop) | $d_1 = 0.0114$ | | |
| $r_2 = \infty$ | $d_2 = 0.0381$ | $n_1 = 1.51633$ | $\nu_1 = 64.15$ |
| $r_3 = \infty$ | $d_3 = 0.6929$ | | |
| $r_4 = 1.6393$ | $d_4 = 0.1425$ | $n_2 = 1.71700$ | $\nu_2 = 47.94$ |
| $r_5 = -0.4835$ | $d_5 = 0.0754$ | | |
| $r_6 = -0.3702$ | $d_6 = 0.0628$ | $n_3 = 1.67270$ | $\nu_3 = 32.10$ |
| $r_7 = 0.5041$ | $d_7 = 0.0911$ | | |
| $r_8 = 1.2477$ | $d_8 = 0.1143$ | $n_4 = 1.51633$ | $\nu_4 = 64.15$ |
| $r_9 = 0.9839$ | $d_9 = 0.1143$ | $n_5 = 1.69680$ | $\nu_5 = 55.52$ |
| $r_{10} = -0.5376$ | $d_{10} = 0.1904$ | | |
| $r_{11} = \infty$ | $d_{11} = 0.0609$ | $n_6 = 1.51633$ | $\nu_6 = 64.15$ |
| $r_{12} = \infty$ | | | |
| $\phi_2 + \phi_3 = -0.33419$, $|r_2/r_1| = 0.29281$ | | | |

Example 7
f = 1.000, F/4.818, IH = 0.112, OB = −19.0402

| | | | |
|---|---|---|---|
| $r_1 = \infty$ (stop) | $d_1 = 0.0114$ | | |
| $r_2 = \infty$ | $d_2 = 0.0381$ | $n_1 = 1.51633$ | $\nu_1 = 64.15$ |
| $r_3 = \infty$ | $d_3 = 0.6928$ | | |
| $r_4 = 1.1878$ | $d_4 = 0.1424$ | $n_2 = 1.71700$ | $\nu_2 = 47.94$ |
| $r_5 = -0.6226$ | $d_5 = 0.0754$ | | |
| $r_6 = -0.3529$ | $d_6 = 0.0628$ | $n_3 = 1.67270$ | $\nu_3 = 32.10$ |
| $r_7 = 0.6151$ | $d_7 = 0.0911$ | | |
| $r_8 = 1.0467$ | $d_8 = 0.1142$ | $n_4 = 1.51633$ | $\nu_4 = 64.15$ |
| $r_9 = 0.5224$ | $d_9 = 0.1142$ | $n_5 = 1.69680$ | $\nu_5 = 55.52$ |
| $r_{10} = -0.6285$ | $d_{10} = 0.1904$ | | |
| $r_{11} = \infty$ | $d_{11} = 0.0609$ | $n_6 = 1.51633$ | $\nu_6 = 64.15$ |
| $r_{12} = \infty$ | | | |
| $\phi_2 + \phi_3 = -0.75458$, $|r_2/r_1| = 0.52416$ | | | |

Example 8

-continued f = 1.000, F/4.818, IH = 0.112, OB = −19.0380

| | | | |
|---|---|---|---|
| $r_1 = \infty$ (stop) | | | |
| | $d_1 = 0.0114$ | | |
| $r_2 = \infty$ | | | |
| | $d_2 = 0.0381$ | $n_1 = 1.51633$ | $\nu_1 = 64.15$ |
| $r_3 = \infty$ | | | |
| | $d_3 = 0.6927$ | | |
| $r_4 = 1.1433$ | | | |
| | $d_4 = 0.1424$ | $n_2 = 1.71700$ | $\nu_2 = 47.94$ |
| $r_5 = -0.6031$ | | | |
| | $d_5 = 0.0754$ | | |
| $r_6 = -0.3293$ | | | |
| | $d_6 = 0.0628$ | $n_3 = 1.67270$ | $\nu_3 = 32.10$ |
| $r_7 = 0.5817$ | | | |
| | $d_7 = 0.0911$ | | |
| $r_8 = 0.9637$ | | | |
| | $d_8 = 0.0762$ | $n_4 = 1.51633$ | $\nu_4 = 64.15$ |
| $r_9 = 0.4782$ | | | |
| | $d_9 = 0.1523$ | $n_5 = 1.69680$ | $\nu_5 = 55.52$ |
| $r_{10} = -0.6157$ | | | |
| | $d_{10} = 0.1903$ | | |
| $r_{11} = \infty$ | | | |
| | $d_{11} = 0.0609$ | $n_6 = 1.51633$ | $\nu_6 = 64.15$ |
| $r_{12} = \infty$ | | | |

$\phi_2 + \phi_3 = -0.85396$, $|r_2/r_1| = 0.52751$

Example 9
f = 1.000, F/4.818, IH = 0.112, OB = −19.0395

| | | | |
|---|---|---|---|
| $r_1 = \infty$ (stop) | | | |
| | $d_1 = 0.0114$ | | |
| $r_2 = \infty$ | | | |
| | $d_2 = 0.0381$ | $n_1 = 1.51633$ | $\nu_1 = 64.15$ |
| $r_3 = \infty$ | | | |
| | $d_3 = 0.6927$ | | |
| $r_4 = 1.0868$ | | | |
| | $d_4 = 0.1424$ | $n_2 = 1.71700$ | $\nu_2 = 47.94$ |
| $r_4 = -0.6133$ | | | |
| | $d_5 = 0.0754$ | | |
| $r_6 = -0.3108$ | | | |
| | $d_6 = 0.0628$ | $n_3 = 1.67270$ | $\nu_3 = 32.10$ |
| $r_7 = 0.6305$ | | | |
| | $d_7 = 0.0911$ | | |
| $r_8 = 0.9439$ | | | |
| | $d_8 = 0.0762$ | $n_4 = 1.51633$ | $\nu_4 = 64.15$ |
| $r_9 = 0.4790$ | | | |
| | $d_9 = 0.1523$ | $n_5 = 1.69680$ | $\nu_5 = 55.52$ |
| $r_{10} = -0.6166$ | | | |
| | $d_{10} = 0.1904$ | | |
| $r_{11} = \infty$ | | | |
| | $d_{11} = 0.0609$ | $n_6 = 1.51633$ | $\nu_6 = 64.15$ |
| $r_{12} = \infty$ | | | |

$\phi_2 + \phi_3 = -0.99533$, $|r_2/r_1| = 0.56432$

Example 10
f = 1.000, F/5.766, IH = 0.1078, OB = −17.9758

| | | | |
|---|---|---|---|
| $r_1 = \infty$ (stop) | | | |
| | $d_1 = 0.0359$ | | |
| $r_2 = -60.2102$ | | | |
| | $d_2 = 0.1078$ | $n_1 = 1.51633$ | $\nu_1 = 64.15$ |
| $r_3 = -0.5123$ | | | |

$|r_2/r_1| = 0.00809$

Example 11
f = 1.000, F/5.766, IH = 0.1080, OB = −18.0205

| | | | |
|---|---|---|---|
| $r_1 = \infty$ (stop) | | | |
| | $d_1 = 0.0360$ | | |
| $r_2 = -2.1836$ | | | |
| | $d_2 = 0.1080$ | $n_1 = 1.61484$ | $\nu_1 = 51.17$ |
| $r_3 = -0.3654$ | | | |
| | $d_3 = 0.0360$ | $n_2 = 1.75520$ | $\nu_2 = 27.51$ |
| $r_4 = -0.4662$ | | | |

$|r_B/r_A| = 0.21350$

Example 12
f = 1.000, F/5.766, IH = 0.1079, OB = −17.9939

| | | | |
|---|---|---|---|
| $r_1 = \infty$ (stop) | | | |
| | $d_1 = 0.0360$ | | |
| $r_2 = 9.0322$ | | | |
| | $d_2 = 0.1079$ | $n_1 = 1.61484$ | $\nu_1 = 51.17$ |
| $r_3 = -0.3396$ | | | |
| | $d_3 = 0.0360$ | $n_2 = 1.75520$ | $\nu_2 = 27.51$ |
| $r_4 = -0.5636$ | | | |

$|r_2/r_1| = 0.06240$

Example 13
f = 1.000, F/4.121, IH = 0.1143, OB = ∞

| | | | |
|---|---|---|---|
| $r_1 = \infty$ (stop) | | | |
| | $d_1 = 0.0114$ | | |
| $r_2 = \infty$ | | | |
| | $d_2 = 0.0381$ | $n_1 = 1.51633$ | $\nu_1 = 64.15$ |
| $r_3 = \infty$ | | | |
| | $d_3 = 0.7544$ | | |
| $r_4 = 1.5769$ | | | |
| | $d_4 = 0.1425$ | $n_2 = 1.71300$ | $\nu_2 = 53.84$ |
| $r_5 = -0.6272$ | | | |
| | $d_5 = 0.0808$ | | |
| $r_6 = -0.4695$ | | | |
| | $d_6 = 0.0629$ | $n_3 = 1.64769$ | $\nu_3 = 33.80$ |
| $r_7 = 0.4695$ | | | |
| | $d_7 = 0.1078$ | | |
| $r_8 = 0.7161$ | | | |
| | $d_8 = 0.1677$ | $n_4 = 1.69680$ | $\nu_4 = 55.52$ |
| $r_9 = -0.7161$ | | | |
| | $d_9 = 0.1677$ | | |
| $r_{10} = \infty$ | | | |
| | $d_{10} = 0.0610$ | $n_5 = 1.51633$ | $\nu_5 = 64.15$ |
| $r_{11} = \infty$ | | | |

$\phi_2 + \phi_3 = -0.24273$, $|r_2/r_1| = 0.39774$ wherein the reference symbols $r_1, r_2, \ldots$ represent radii of curvature on the surfaces of the respective lens components, the reference symbols $d_1, d_2, \ldots$ designate thicknesses of the respective lens components and airspaces reversed therebetween, the reference symbols $n_1, n_2, \ldots$ denote refractive indices of the respective lens components and the reference symbols $\nu_1, \nu_2, \ldots$ represent Abbe's numbers of the respective lens components.

Figure 10:
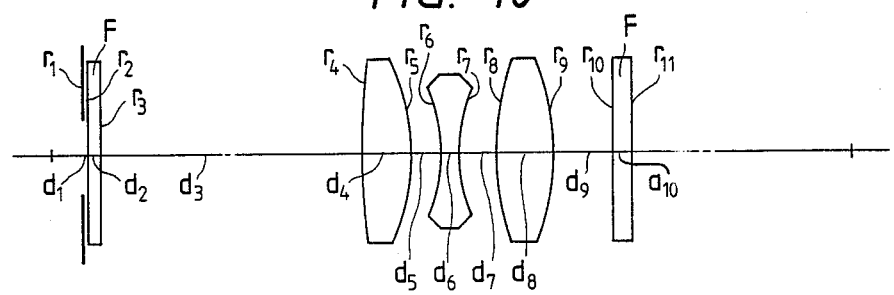
FIG. 10 through FIG. 13 show sectional views illustrating examples of the imaging lens used in the present invention.
Figure 14:
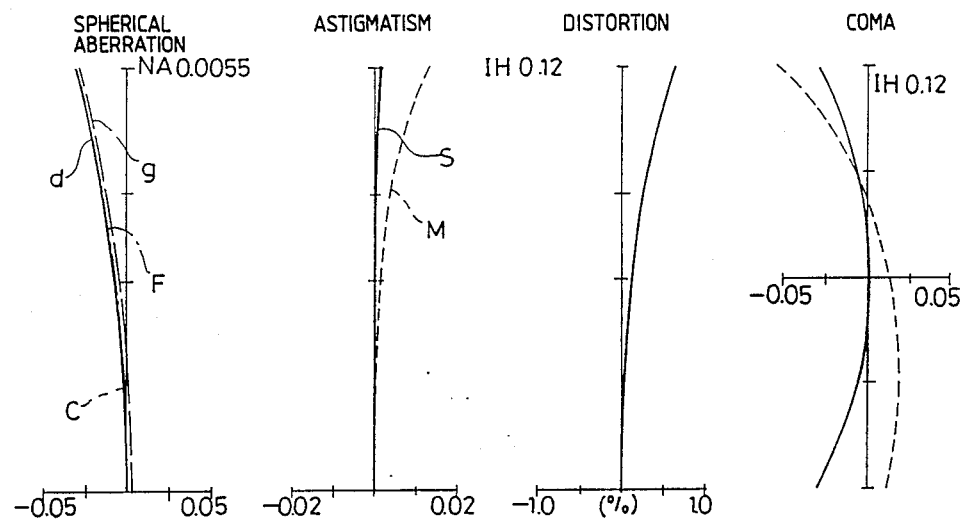
FIG. 14 through FIG. 26 show curves illustrating aberration characteristics of Examples 1 through 13 of said image pickup lens.
Figure 15:
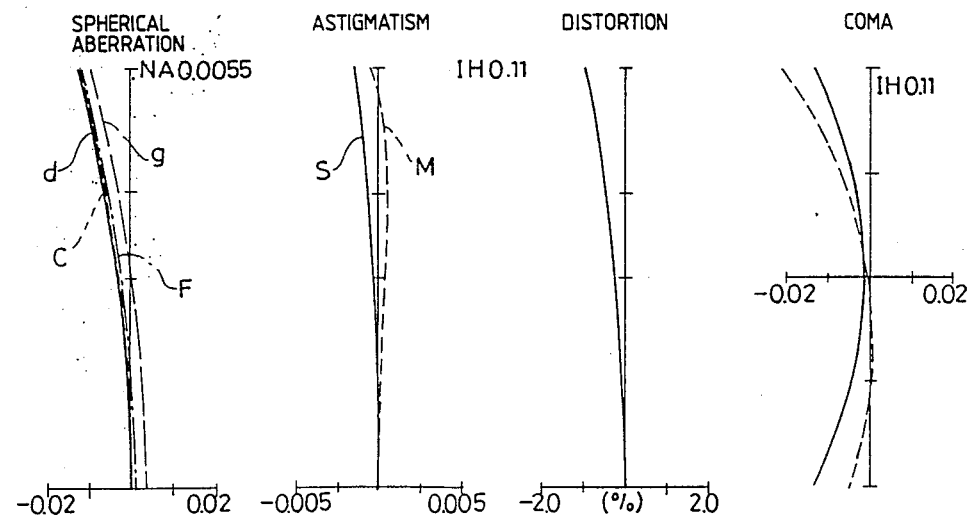
Figure 26:
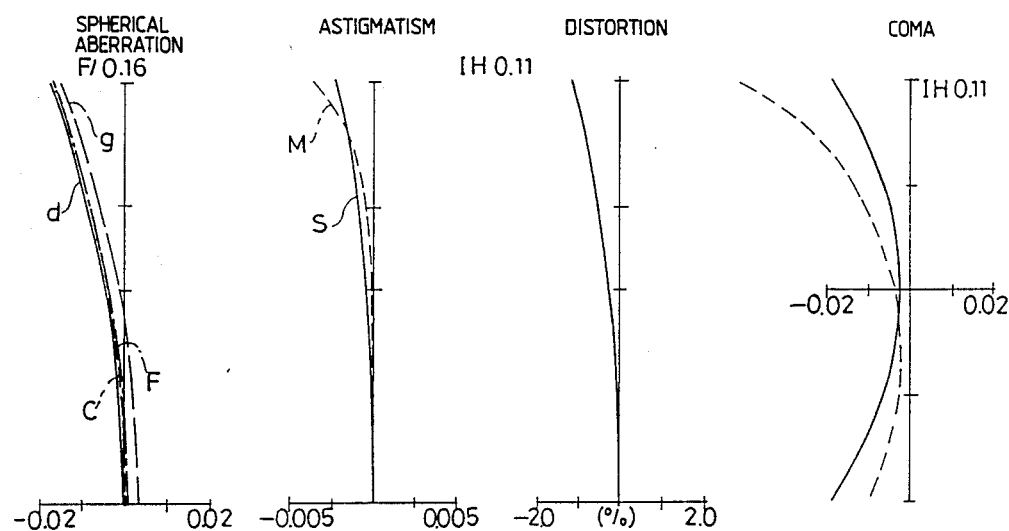

The Examples 1, 2 and 13 are triplet type imaging optical systems having the composition shown in FIG. 10, and have the aberration characteristics illustrated in FIG. 14, FIG. 15 and FIG. 26 respectively. As in understood from the curves illustrating the aberration characteristics, these Examples are so designed as to produce the spherical aberration in the negative direction.

Figure 16:
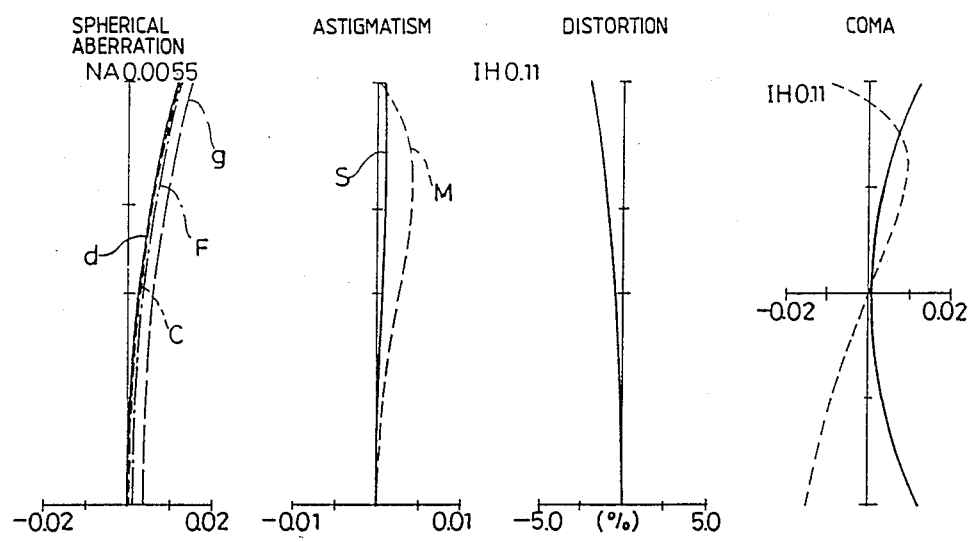
Figure 17:
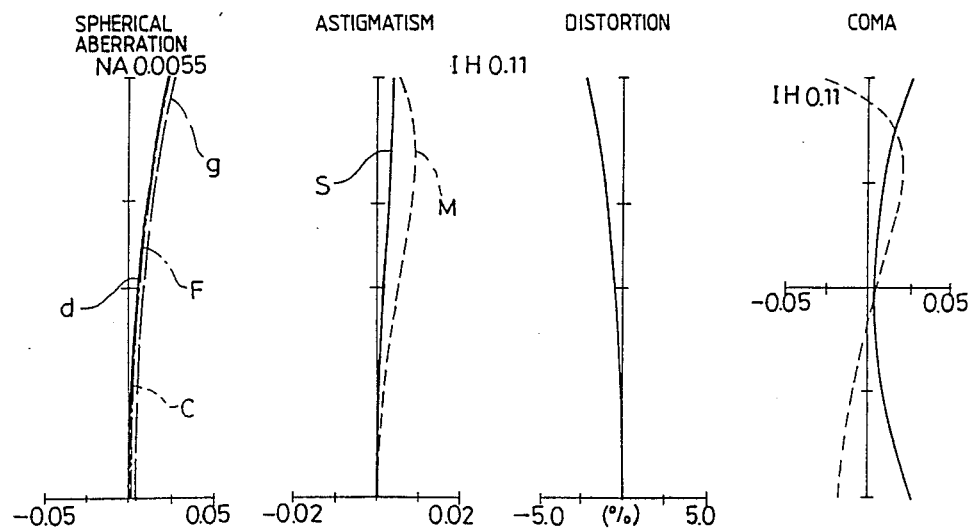
Figure 18:
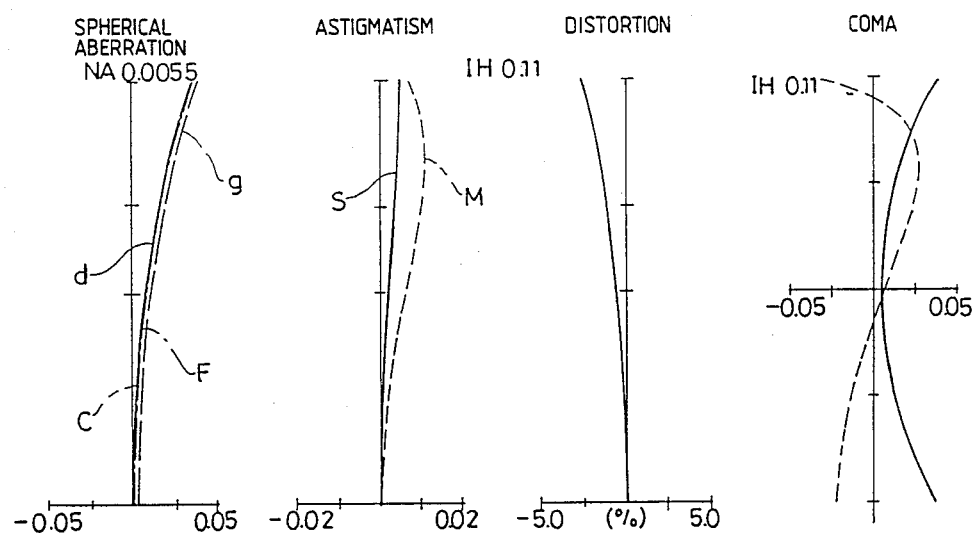

The Examples 3, 4 and 5 are also the triplet type imaging optical systems having the composition shown in FIG. 10. However, these Examples are so designed as to produce the spherical aberration in the positive direction as illustrated in FIG. 16, FIG. 17 and FIG. 18 respectively.

Figure 11:
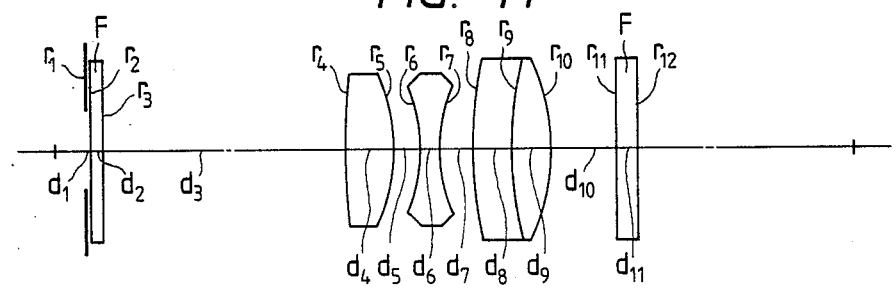
Figure 19:
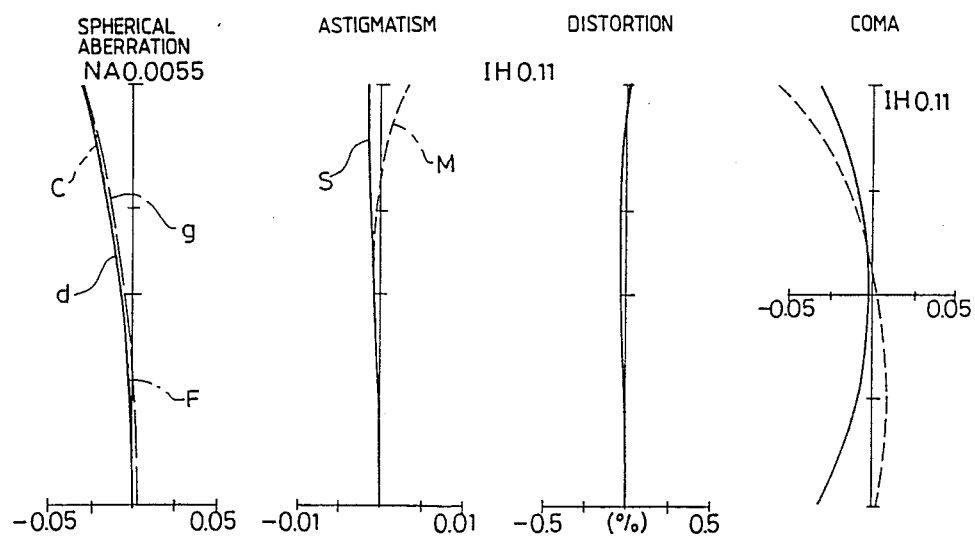

The Example 6 is a Tesser type imaging optical system having the composition shown in FIG. 11 and so designed as to produce the spherical aberration in the negative direction as seen from the aberration characteristics illustrated in FIG. 19.

Figure 20:
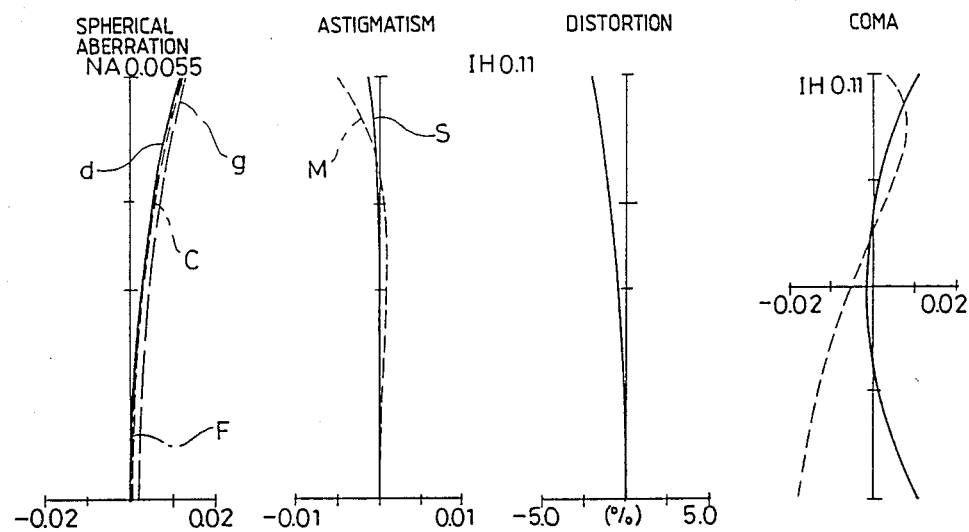
Figure 21:
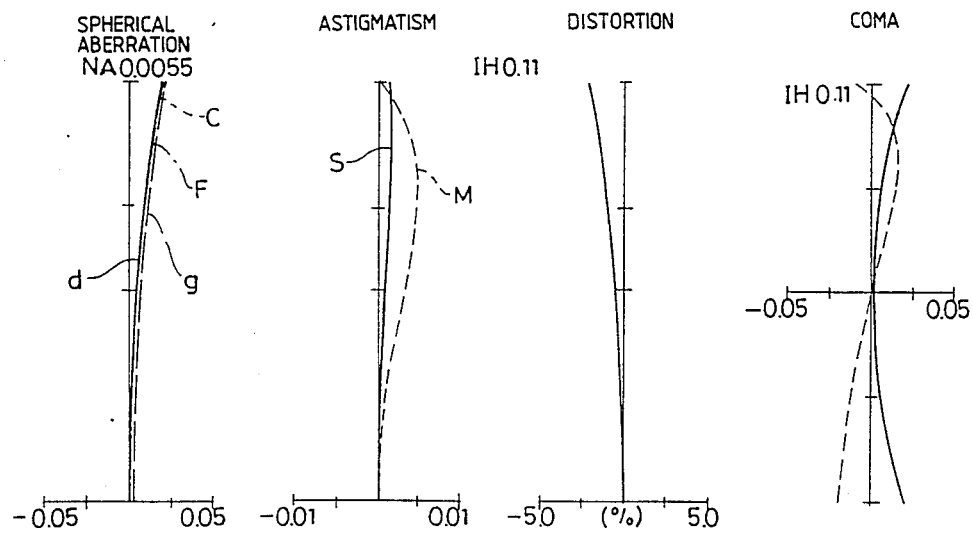
Figure 22:
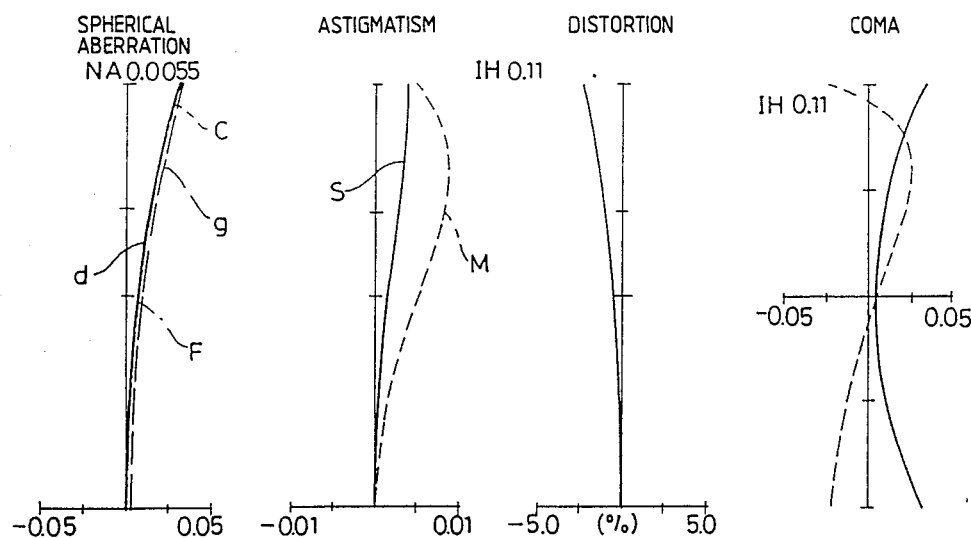

The Examples 7, 8 and 9 are also the Tesser type imaging optical systems having the composition illustrated in FIG. 11. However, all of these Examples are so designed as to produce the spherical aberration in the positive direction as seen from the aberration characteristics illustrated in FIG. 20, FIG. 21 and FIG. 22.

Figure 12:
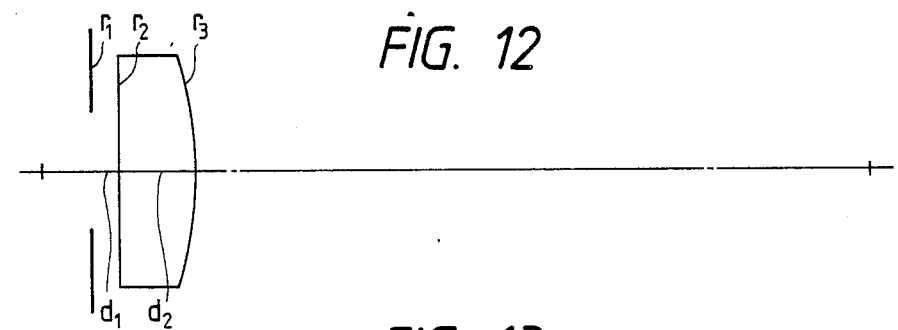
Figure 23:
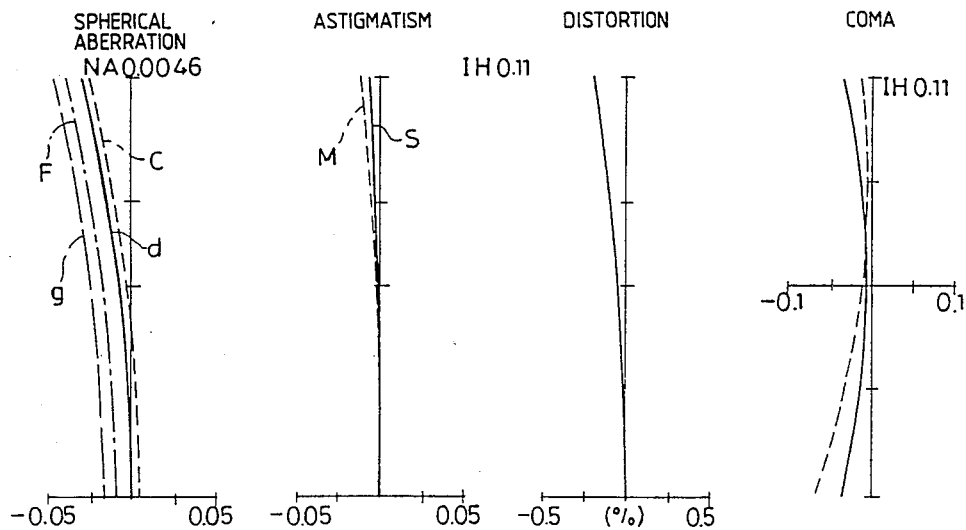

The Example 10 is an imaging optical system consisting only of a single lens component as shown in FIG. 12 and is so designed as to produce the spherical aberration in the negative direction as is understood from the aberration characteristics visualized in FIG. 23.

Figure 13:
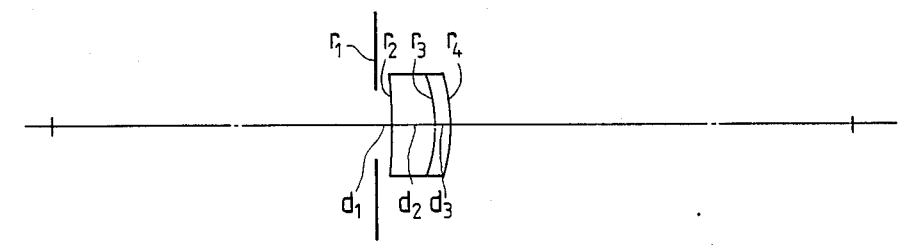
Figure 24:
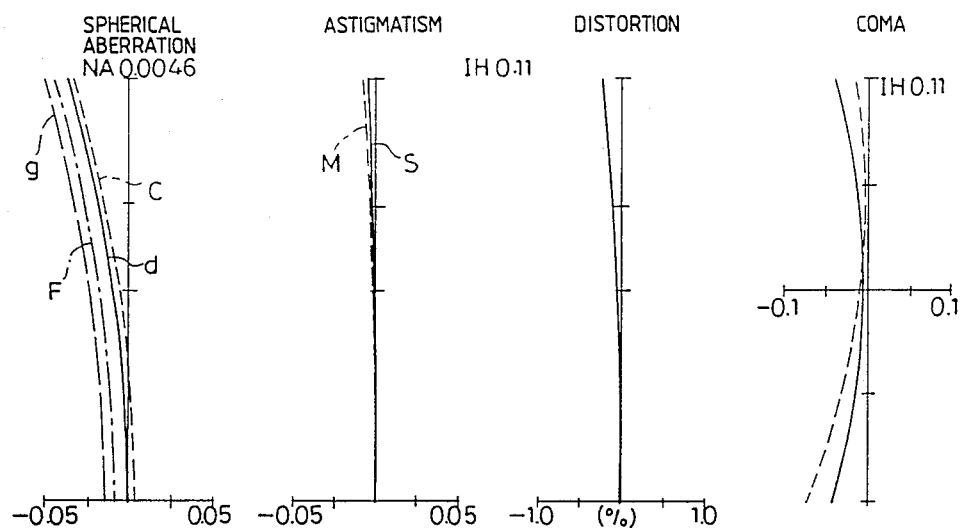
Figure 25:
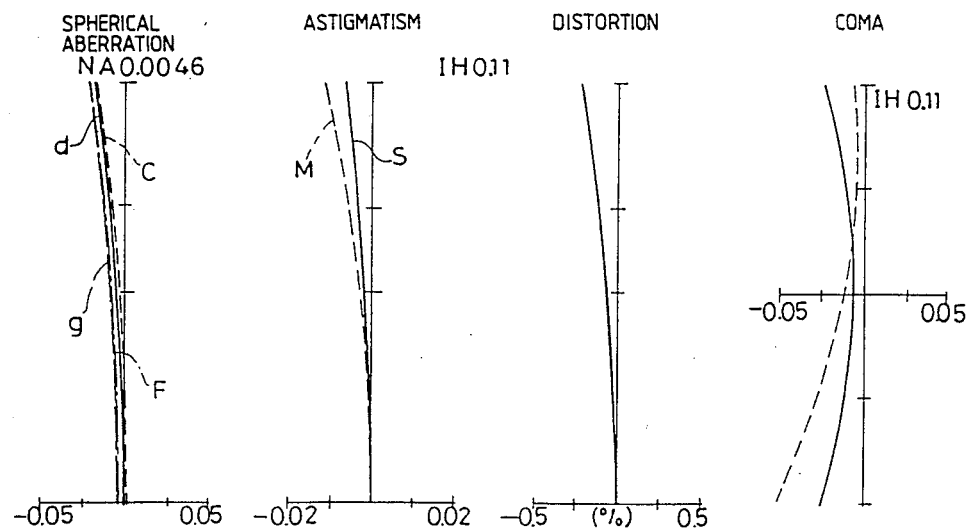

The Examples 11 and 12 are imaging optical systems consisting of an achromatic doublet shown in FIG. 13, and have the aberration characteristics visualized in FIG. 24 and FIG. 26 respectively. The spherical aberration is produced in the negative direction in each of these Examples. In addition, the reference symbol F represents a filter in the sectional views illustrating the imaging optical systems.

In most of the fiberscopes practically used in the present days, the frequencies, etc. produced by diameters of the image fibers are within a range of 10 to 30 lines/mm on the image planes. For the fiberscope using the finest image fiber producing a frequency of 30 lines/mm, it is therefore necessary to design the imaging optical system so as to satisfy the conditions of the present invention.

The optical systems described above as the Examples satisfy all these conditions and are usable in the TV camera for endoscopes according to the present invention.

Since the rotating member 4 for allowing the TV camera to be freely rotated around the optical axis is adopted in addition to the special imaging lens described above, the embodiment of the present invention has a higher effect to prevent the moiré

Further, the moiré are produced due to the fact that the picture elements in the image guide fiber bundle and the picture elements of the image sensor are arranged regularly. Accordingly, level of the moiré to be produced is varied by changing the angle formed between arrangement directions of both types of the picture elements. It is therefore possible to adjust the angle formed between the arrangement directions, when the TV camera for endoscopes comprises at least an image sensor, by allowing said image sensor to be rotated with regard to a fiberscope with a rotating member, for example, as that shown in FIG. 2. The moiré to be produced can be adjusted by this means.

Furthermore, the embodiment of the present invention comprises the optical low pass filter which can provide more excellent effect to prevent the moiré

Figure 8:
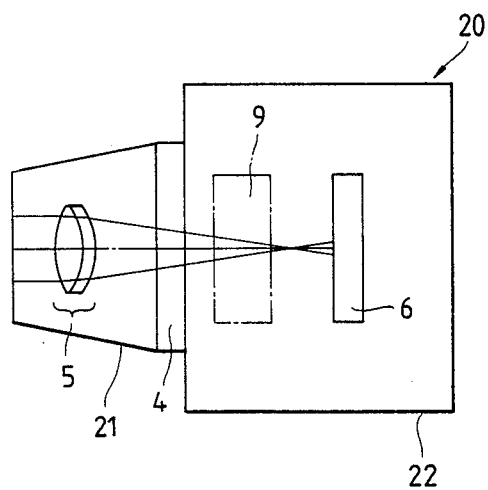
FIG. 8 shows a sectional view illustrating a TV camera designed as an adapter.

Moreover, the moiré are produced, though at different levels, in almost all fiberscopes. Therefore, it is desirable to control production of the moiré to a minimum level by adjusting the diameter of the circle of confusion on the imaging plane of the image sensor with the design of the imaging optical system for a fiberscope producing the moiré at a relatively low level, and to eliminate the remaining moiré by utilizing the rotation described above and arranging an optical low pass filter. In other words, it is desirable to correct the remaining moiré by rotating the TV camera with the rotating member 4 shown in FIG. 2. Alternately, it is desirable to design the TV camera to be attached to the eyepiece side of a fiberscope in two separate units of an imaging adapter 21 equipped with the imaging lens 5 and a camera body 22 connected by way of the rotating member 4. In this case, it is possible to removably or exchangeably arrange the optical low pass filter 9 before the image sensor 6 in the camera body 22. In case of the composition illustrated in FIG. 8, both the imaging adapter 21 and the camera body 22 can be exchanged with others. It is therefore possible to exchange the imaging lens with a different attachment. Further, it is possible to exchange only the optical low pass filter in the camera body or replace the camera body proper with another comprising a different optical low pass filter.

Let us represent the highest frequency by $\nu_{max}$ and the lowest frequency by $\nu_{min}$ out of the cut-off frequencies determined depending on fiber diameter, as measured on the images transferred through the image guide fiber, of the fiber scopes to be used. It is sufficient to select, within the range between these frequencies ($\nu_{min}$ and $\nu_{max}$), the cut-off frequency determined by the minimum circle of confusion and the cut-off frequency determined by thickness of the quartz plate which are different from each other.

FIG. 9A through FIG. 9B show graphs illustrating the cut-off frequencies $\nu_{min}$ and $\nu_{max}$ determined depending on fiber diameters, the cut-off frequencies of the optical low pass filters used and contrast obtained therewith.

In these drawings, the reference symbol a indicates the MTF curves which is zeroed at the frequency determined depending on the diameter $D_0$ of the minimum circle of confusion, the reference symbol b indicates the MTF curves of the optical low pass filters and the reference symbol c indicates the a composite curves of both the types of curves.

In FIG. 9A, the MTF is zeroed at the frequency $\nu_{max}$ on the curve a, whereas the cut-off frequency is located at $\nu_{min}$ on the curve b. A curve obtained as a composite of these curves is shown as the curve c in FIG. 9B.

In FIG. 9C, the MTF is zeroed at the frequency $\nu_{min}$, whereas the cut-off frequency is located at $\nu_{max}$ on the curve b. A composite curve of these curves is also as shown in FIG. 9B.

In FIG. 9D, the MTF is zeroed at $\nu_{max}$ on the curve a, whereas the curve b has the cut-off frequency between $\nu_{min}$ and $\nu_{max}$ A composite of these curves is illustrated in FIG. 9E.

By using a combination of an imaging lens having the spherical aberration and an optical low pass filter as described above, it is possible to control the spatial frequency of the optical system used in the TV camera to a very low value within a desired spatial frequency range and obtain a remarkable effect to prevent the moiré

Figure 7:
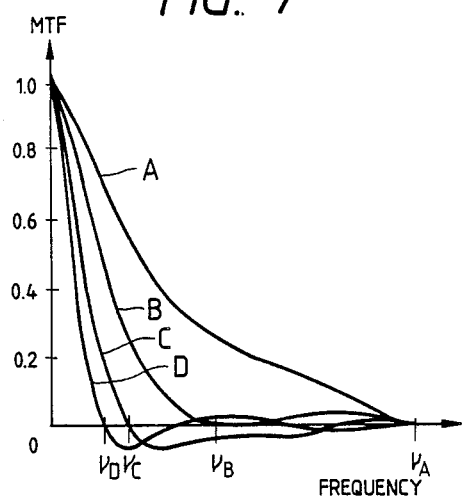
FIG. 7 shows graphs illustrating the MTF when the imaging optical system is placed out of focus.

Now, the Embodiment 2 of the TV camera for endoscopes according to the present invention will be described below. Speaking concretely, the Embodiment 2 is so adapted as to prevent the moiré from being produced by adjusting the distance between the position of the image formed by the eyepiece lens 3 and the imaging lens 5 after transferring from the end surface of the image guide fiber bundle and the imaging plane 6a of the image sensor 6 along the optical axis in the TV camera for endoscopes having the composition shown in FIG. 2. In other words, out-of-focus degree is adjusted by adjusting the distance between the imaging plane I to the imaging plane 6a so as to be gradually increased from zero. This adjustment allows to vary the spatial frequency at which the contrast (MTF) is zeroed. That is to say, the above-mentioned spatial frequency is gradually lowered as out-of-focus degree is enhanced. In FIG. 7, the curve A corresponds to a case where the out-of-focus degree is zero and the curves B through D correspond to out-of-focus degrees gradually increasing. Contrast is zeroed at the frequencies $\nu_A$, $\nu_B$, $\nu_C$ and $\nu_D$ on the curves A, B, C and D respectively. It is therefore possible to prevent the moiré from being produced by selecting an out-of-focus degree so as to coincide the spatial frequency determined by fiber arrangement in the image guide fiber bundle with the spatial frequency at which the contrast due to the out-of-focus condition is zeroed. In other words, it is possible to obtain the effect to eliminate the moiré by determining the above-mentioned out-of-focus degree in accordance with the fiber diameter of the fiberscope to be used, etc.

The moiré are produced due to the regular arrangements of the picture elements in the exit end surface of the image guide fiber bundle and the picture elements in the imaging surface. Accordingly, produced condition of the moiré is varied when the arrangement directions of the above-mentioned two types of picture elements is relatively varied by rotating the TV camera 20 relatively to the fiberscope 10, for example, with the rotating member 4 arranged in the TV camera for endoscopes shown in FIG. 2. Production of the moiré can be minimized by adopting a design allowing the adjustment of the angle between the two types of picture elements with such a rotating member.

The two types of adjustments described above makes it possible to prevent production of the moiré most effectively in accordance with a fiberscope attached to the TV camera.

Further, the moiré are produced, though at different levels, in almost all TV cameras using fiberscopes. Therefore, it is effective to control production of the moiré to a minimum level by using an optical low pass filter in combination with a fiberscope in which the moiré are produced relatively at a low level, and then eliminate the moiré by the two types of adjustments described above. Speaking concretely, it is sufficient to fix an optical low pass filter having a cut-off frequency in the vicinity of $\nu_{max}$ which is the highest of the spatial frequencies $\nu$, determined by a fiber diameter of a fiberscope out of a plural number of fiberscopes to be combined, of an image transferred through the image guide fiber bundle and formed by an imaging optical system on the image sensor, and then eliminate the moiré produced at lower frequencies by the out-of-focus adjustment and the adjustment of the relative angle described above.

The means and adjustments described above are illustrated in FIG. 32A and FIG. 32B. In these drawings, the spatial frequency is taken as the abscissa and the MTE is taken as the ordinate. In these drawings, the curves traced in the dashed lines visualize the relations between the frequency and the MTF when an optical low pass filter consisting of a quartz plate is arranged in the optical path, the curves traced in the chain lines visualize the relations between the frequency and the MTF when the imaging lens is placed in the out-of-focus condition, and the curves traced in solid lines visualize the relations between the frequency and the MTF when an optical low pass filter is arranged and further the imaging lens is placed in the out-of-focus condition.

Figure 32A:
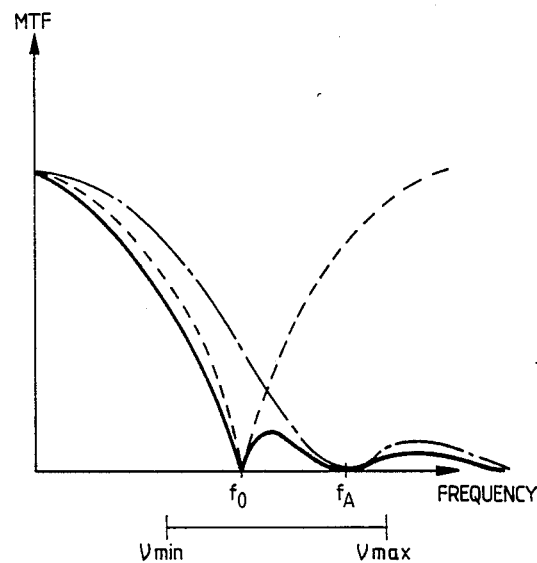
FIG. 32A and FIG. 32B show graphs illustrating relations of the MTF versus frequencies when low pass filters are arranged and when the imaging lens are placed out of focus.
Figure 32B:
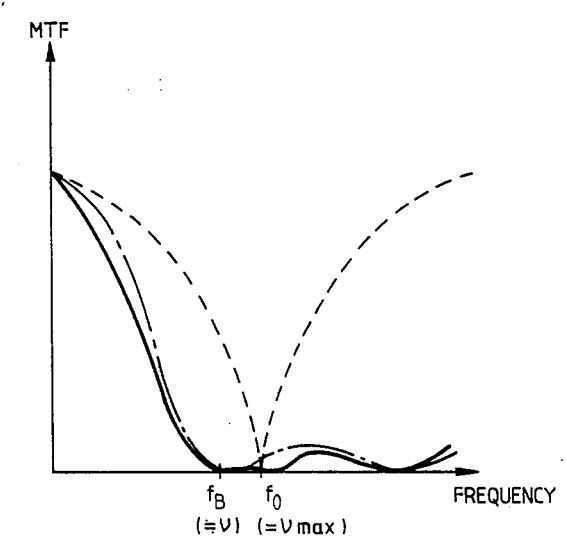

When the cut-off frequency $f_0$ of an optical low pass filter is set at $\nu_{max}$ in a case where the frequencies $\nu$ determined by the fiber diameter is lower than $\nu_{max}$ ($\nu < \nu_{max}$) as shown in FIG. 32B, the MTF is very low at the frequencies higher than $\nu$ and the moiré can be corrected very effectively by placing the imaging lens in such an out-of focus condition as to make the frequency $f_B$ at which the MTF is zeroed is nearly equal to $\nu$.

The effect to prevent the moiré can be obtained by preliminarily determining the cut-off frequency $f_0$ of an optical low pass filter at an adequate valve between $\nu_{min}$ and $\nu_{max}$ as shown in FIG. 32A, and adjust the cut-off frequency $f_A$ so as to obtain $f_0 < f_A$ in case of $f_0 < \nu$ or $f_A > f$ in case of $f_0 > \nu$ by placing the imaging lens in the out-of focus condition. In case of $f_0 < \nu$, however, resolution is degraded since response is zeroed at the frequencies lower than the frequency $\nu$ determined depending on fiber diameter.

Now, description will be made on the relation between the frequency at which the image contrast (MTF) is zeroed and the out-of-focus degree.

Let us assume that an imaging optical system consisting of an eyepiece lens and an imaging lens is an ideal aplanatic optical system. When the out-of-focus degree from the imaging position is D, spot diameter $\Phi$ of a point image is given by the following formula:

$$\Phi = D/F_{n0}$$

wherein the reference symbol $F_{n0}$ represents F number of the imaging optical system and $\sin \theta$ is assumed to be nearly equal to $\tan \theta$. The frequency $\nu$ at which the contrast (MFT) is zeroed by the circular spot having the diameter $\Phi$ is given by the following formula:

$$\nu = 1.22/\Phi = 1.22 F_0/D$$

In the TV camera for endoscopes shown as the Embodiment in FIG. 2, the position of the imaging plane of the imaging lens 5 and the imaging plane of the image sensor 6 relative to the optical axis are adjusted by shifting the imaging lens 5 along the optical axis. The out-of-focus degree is varied by this adjustment. It is therefore possible to select an out-of-focus degree optimum for zeroing the image contrast (MTF) at the spatial frequency determined by fiber diameter of image guide fiber bundle of a fiberscope. Accordingly, it is possible to prevent the moiré from being produced.

Further, it is possible to adjust the relative angle between arrangement direction of the picture elements in the exit end surface of the fiber bundle and arrangement direction of the picture elements in the imaging surface of the solid-state image sensor by rotating the TV camera 20 relatively to the fiberscope 10 with the rotating member 4. This means permits adjusting so as to control the moiré to be produced at a minimum level.

Figure 27:
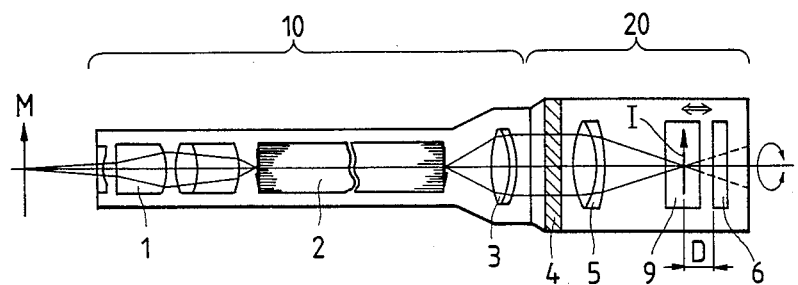
FIG. 27 through FIG. 31 show sectional views illustrating Embodiments 2 through 6 of the TV camera for endoscopes according to the present invention.

FIG. 27 shows the Embodiment 2 of the present invention wherein production of the moiré is prevented by placing the imaging optical system in an out-of-focus condition. In this embodiment, an optical low pass filter 9 consisting of a quartz plate or the similar material is arranged on the optical axis at a location before the image sensor 6 in the TV camera 20. The out-of-focus degree is adjusted by shifting the image sensor 6 integrally with the optical low pass filter 9 along the optical axis so as to vary the distance between the imaging position and the imaging plane.

Figure 33:
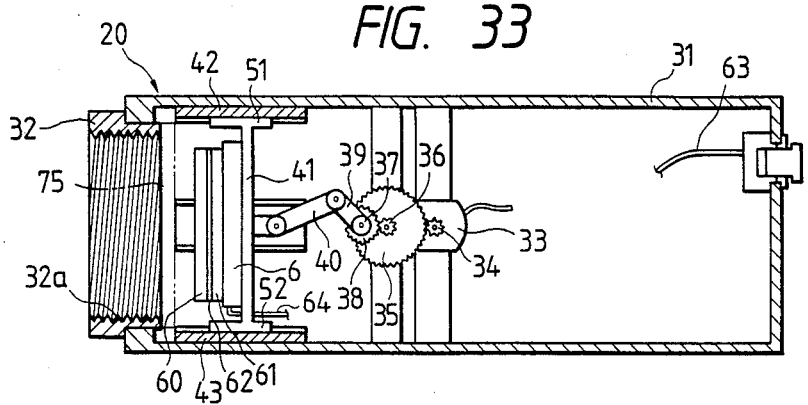
FIG. 33 through FIG. 35 show sectional views illustrating mechanisms for shifting the image sensor in the TV camera according to the present invention.
Figure 36:
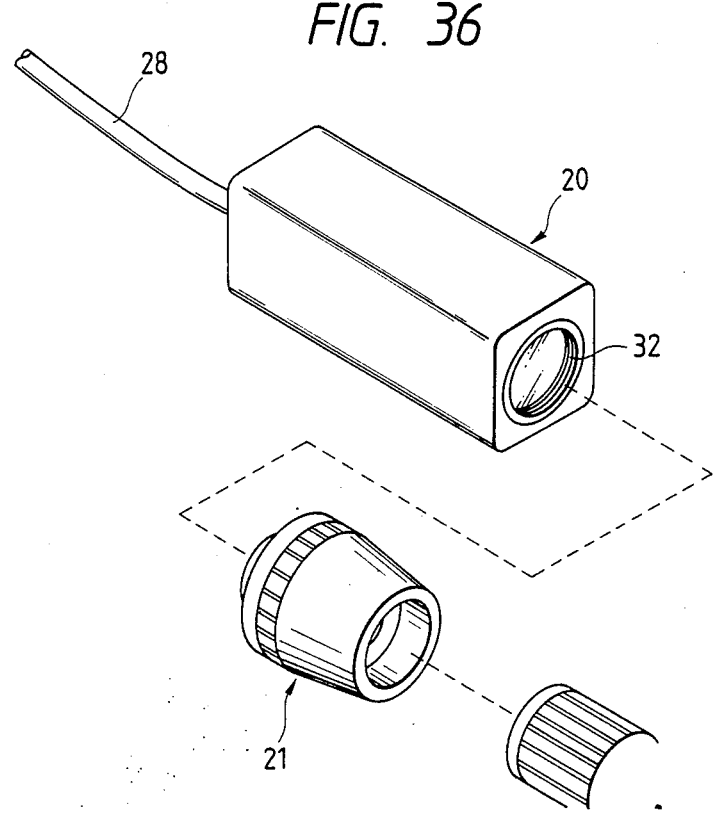
FIG. 36 shows perspective view schematically illustrating the TV camera according to the present invention.

FIG. 33 shows a sectional view illustrating a mechanism for shifting the image sensor and the optical low pass filter of the TV camera, and FIG. 36 shows an external view of the cameras. Attached to the front end surface of the outer casing 31 of the camera body is a mount 32 having an aperture 32a threaded inside. Disposed inside the outer casing 31 is a motor 33 having a rotating shaft to which a gear 34 is attached. Engaged with the gear 34 is a reduction gear 35, which is in turn engaged with a gear 36 attached coaxially with the gear 35 and a gear 38 attached to a crankshaft 37. Connected to the crankshaft 37 are crankshafts 39 and 40, and a slide member 41 for mounting the solid-state image sensor 6 is attached to the tip of the shaft 40. The slide member 41 is supported so as to be slidable in the longitudinal direction of the camera by feet 51 and 52 kept in contact with shallow U-shaped guide members 42 and 43 arranged on the inside surface of the outer casing 31. Attached to the slide member 41 are the solid-state image sensor 6 in the direction facing the aperture of the mount 32, an optical low pass filter consisting of three quartz plates 60 and 61 laminated thereon, and an infrared cut filter 62.

The motor 33 is controlled with a focus switch (seesaw switch) by way of a signal line 63. A signal line 64 of the image sensor 6 is connected to an external apparatus by way of a connector. This TV camera is set in position by attaching an adapter 21 comprising an imaging lens to the eyepiece of the fiberscope and screwing the connector of the adapter 21 into the mount 32 of the camera 20.

Figure 37:
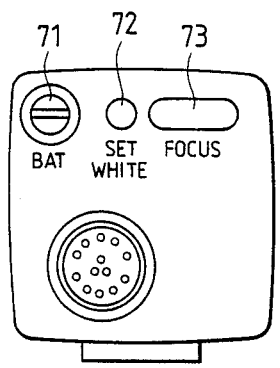
FIG. 37 shows a rear view of the TV camera according to the present invention.

FIG. 37 shows a rear view of the TV camera 20 on which a battery checker 71, a white balance set button 72 and a focus switch 73 are arranged. When the focus switch is turned on one side, the motor 33 rotates in the normal direction to advance the slide member 41 by way of the gears 34, 35, 36 and 38 as well as the crankshafts 39 and 40. When the focus switch is turned on the other side, the motor 33 rotates in the reverse direction to move the slide member 41 backward. Therefore, out-of-focus condition of an image on the solid-state image sensor can be controlled as desired. Waterproof effect is obtained by arranging a glass plate 75 so as to close the aperture of the mount 32 as shown in the chain line in FIG. 33 as occasion demands.

Since this embodiment is equipped with the optical low pass filter, it the moiré within a minimum range out of the moiré produced by the plural number of fiberscopes to be attached by using the filter, and further eliminates the moiré by adjusting the out-of-focus condition of the imaging lens and relative angle between the arrangement directions of the picture elements in accordance with a fiberscope attached to the TV camera.

Figure 28:
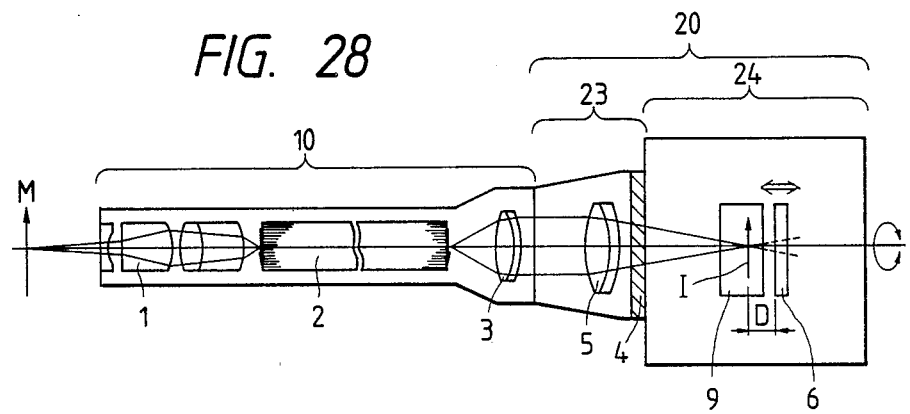

FIG. 28 illustrates the Embodiment 3 of the TV camera which is so designed as to be separable into an imaging adapter 23 having the imaging lens 5, and an imaging section comprising the image sensor 6 and the optical low pass filter 9. This design makes it possible to replace the imaging adapter 23 with another comprising an imaging lens having a different magnification. In this case, the out-of-focus degree required for preventing production of the moiré is largely variable since the number of the combinations of fiberscopes and imaging adapters is increased. For combinations producing the moiré at relatively low levels, however, the moiré are eliminated by the optical low pass filter. For combinations producing the moiré at high levels, it is possible to eliminate the moiré by adjusting the out-of-focus degree and the relative angle between the arrangement directions of the picture elements in addition to the elimination of the moiré by the optical low pass filter.

Figure 29:
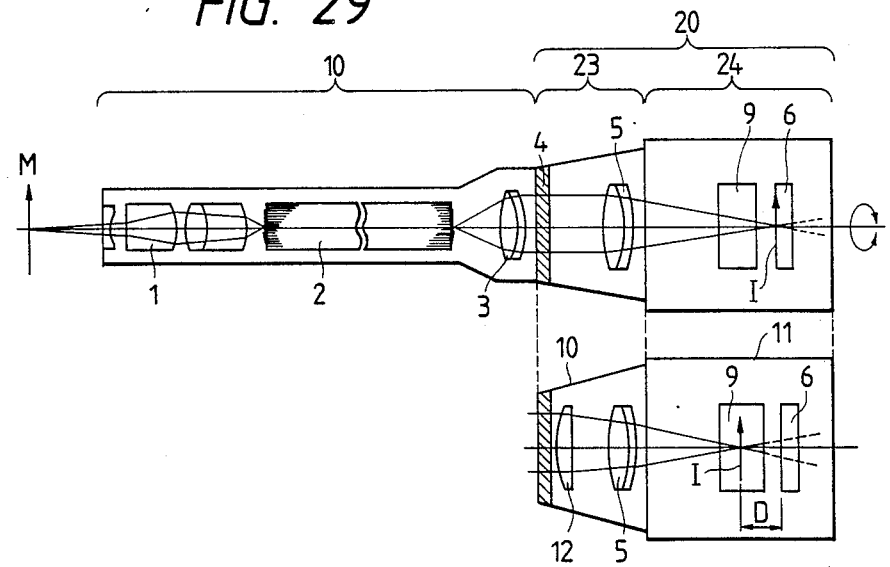

FIG. 29 illustrates the Embodiment 4 of the TV camera according to the present invention wherein an out-of-focus lens 12 having relatively weak refractive power is removably arranged before the imaging lens 5. When the out-of-focus lens is removed, an image on the exit end surface of the image guide fiber bundle is focused on the imaging surface by the imaging lens 5. The moiré are eliminated by inserting the out-of-focus lens in position. It is possible to eliminate the moiré effectively by preparing a plural number of out-of-focus lenses having different refractive powers and using an out-of-focus lens which is optimum for a fiberscope attached to the TV camera. The Embodiment 4 is the same as the Embodiment 3, except for the facts that the rotating member 4 is arranged on the side of the fiberscope of the imaging adapter 23 and that the imaging lens is kept fixed.

Figure 30:
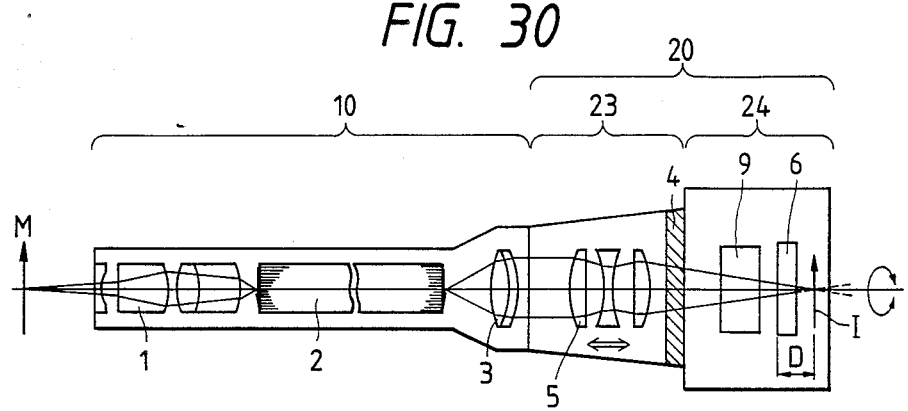

FIG. 30 shows the Embodiment 5 of the TV camera according to the present invention wherein the imaging lens is designed as a vari-focal lens. The Embodiment 5 is so adapted as to increase out-of-focus degree as magnification of the imaging lens 5 is enhanced. That is to say, as magnification of the imaging lens is enhanced, an image of fiber formed on the imaging surface has a larger diameter and lower frequency. In other words, the Embodiment 5 is so adapted as to prevent production of the moiré by increasing out-of-focus degree as magnification is enhanced. In other respects, the Embodiment 5 is the same as the Embodiment 3, except for the fact that the image sensor 6 and the optical low pass filter are kept fixed.

Figure 31:
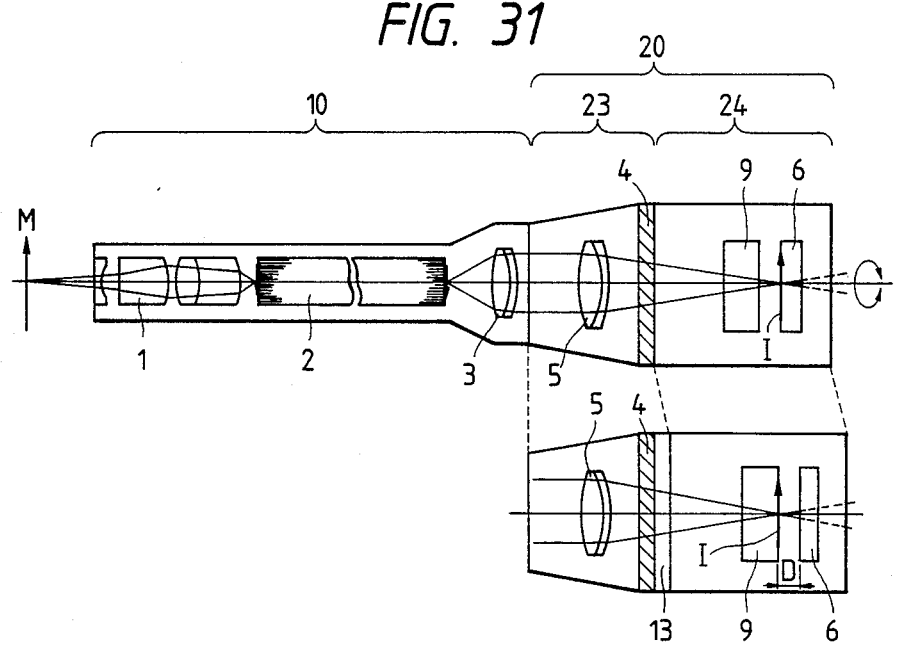

FIG. 31 illustrates the Embodiment 6 of the TV camera according to the present invention. In this embodiment, a ring 13 having definite thickness is arranged between the imaging adapter 23 and the imaging section, whereby an image is placed in out-of-focus condition by varying the optical path length between the imaging lens 5 and the image sensor 6. The out-of-focus degree can be varied by preparing a plural number of rings having different thickness and replacing the rings with one another. In other respects, the Embodiment 6 is the same as the Embodiment 3, except for the fact that the image sensor and the optical low pass filter are kept fixed.

Figure 34:
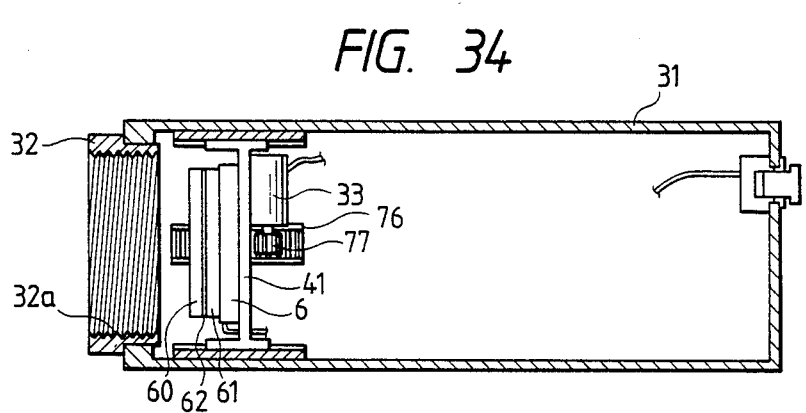

It is possible, for shifting the solid-state image sensor, to adopt the mechanisms described below. FIG. 34 shows a mechanism designed in such a manner that the foot 52 is prolonged, a rack 76 is formed on the top surface thereof and the slide member 41 is driven directly by a pinion 77 attached to the motor 33.

Figure 35:
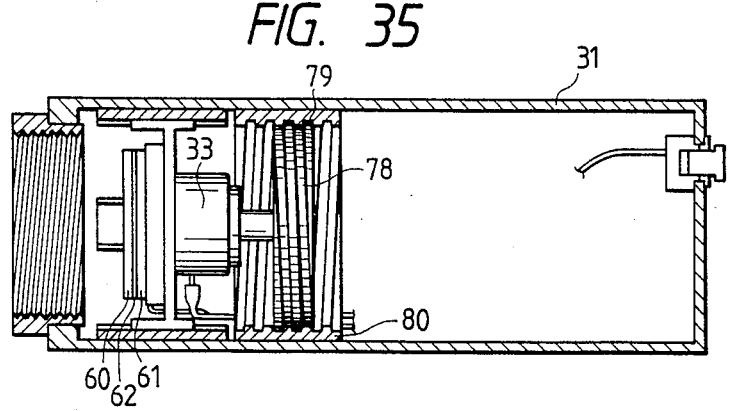

FIG. 35 shows a mechanism wherein the motor 33 is attached to the slide member 41, revolving member 78 is fixed to the rotating shaft of the motor 33, a helicoid screw 80 is fixed inside the outer casing 31, and the helicoid screw 80 is engaged with thread formed on the outer circumferential surface of the revolving member 78. The mechanism shown in this drawing is so adapted as to revolve the revolving member 78 by rotation of the motor 33, thereby shifting the slide member 41, motor 33 and the revolving member 78. Accordingly, the solid-state image sensor 6 is moved back and forth together with the slide member 41. The image sensor to be used in the TV camera according to the present invention may be an imaging tube or a solid-state image sensor such as CCD or MOS. Further, the imaging system may be of the color type or monochromatic type.

In addition, the means for preventing production of the moiré adopted by the present invention is applicable also for eliminating the moiré and false color signals in the general TV cameras, electronic cameras, electronic endoscopes, electronic non-flexible endoscopes and so on. In such cases, diameters of the minimum circles of confusion and out-of-focus degrees should desirably be selected not based on the cut-off frequencies of image guide fiber bundles in imaging optical systems but in accordance with sampling frequencies of image sensors and mosaic filters. For example, the frequency $\nu$ defined by the condition (1) for determining a range of diameter of the minimum circle of confusion in an imaging optical system should desirably be determined as ½ of a sampling frequency of an image sensor or a mosaic filter.

As is understood from the foregoing description, the TV camera for endoscopes according to the present invention is simple in the composition thereof, compact in the dimensions thereof and manufacturable at a low cost owing to the design to adjust the diameter of the minimum circle of confusion to a predetermined size on the image formed on an imaging surface by an image forming optical system as well as the design to deviate the image position for a predetermined distance from the imaging surface by placing the image in an out-of-focus condition, and is capable of permitting to observe images with excellent resolution and contrast while preventing production of the moiré

We claim:

1. A television camera for endoscopes for photographing an image of an object formed on an exit end face of an image guide fiber bundle included in said endoscopes, comprising:

an image sensor, an imaging lens system for focusing the image of said object onto a light receiving surface of said image sensor, said imaging lens system having some aberration to impart a degree of blurring, and an optical low pass filter between said exit end face of said image guide and said image sensor;

said television camera being arranged so that the relative position of the image formed by said imaging lens system and said light receiving surface is adjustable along the optical axis of said imaging lens system so as to satisfy the following condition (1):

$$D_0 \geqq 0.6/\nu \quad (1)$$

wherein reference symbol $D_0$ represents a diameter of a circle of confusion on said light receiving surface, and reference symbol $\nu$ represents a spatial frequency determined by a diameter of unit fiber of said image guide fiber bundle or the spatial frequency corresponding to the Nyquist frequency of said image sensor.

2. A television camera for endoscopes according to claim 1 wherein the relative angle formed between the arrangement direction of the fibers on the exit end surface of said image guide fiber bundle and the arrangement direction of the picture elements on said imaging surface is adjustable.

3. A television camera for endoscopes according to claim 1 wherein said optical low pass filter is composed of at least a quartz plate.

4. A television camera for endoscopes according to claim 1 wherein said television camera comprises an imaging adapter including said imaging lens system and a camera body including said image sensor.

5. A television camera for endoscopes according to claim 4 wherein a plural number of attachment rings having different lengths in the direction of the optical axis are removably and exchangeably arranged between said imaging lens adapter and said camera body.

6. A television camera for endoscopes according to claim 1 wherein said image sensor is arranged movable along the optical axis.

7. A television camera for endoscopes according to claim 1 wherein said imaging lens system includes a plurality of lens components with at least one lens component being movable along the optical axis.

8. A television camera for endoscopes according to claim 1 wherein a lens component having refractive power weaker than that of said imaging lens system is removably arranged on the optical axis.

9. A television camera for endoscopes according to claim 1 wherein said imaging lens system has variable magnification, and deviation between an image position of said imaging lens system and said light receiving surface is gradually increased as magnification of said imaging lens system is enhanced.

10. A television camera for endoscopes according to claim 1 wherein said imaging lens system comprises a first lens component having positive refractive power, a second lens component having negative refractive power and a third lens component having positive refractive power, and is so designed as to satisfy the following condition (2):

$$\Phi_2 + \Phi_3 > -0.5 \quad (2)$$

wherein reference symbol $\Phi_2$ represents refractive power of an image side surface of the first lens component and reference symbol $\Phi_3$ designates refractive power of an object side surface of the second lens component.

11. A television camera for endoscopes according to claim 1 wherein said imaging lens system comprises a first lens component having positive refractive power, a second lens component having negative refractive power and a third lens component having positive refractive power, and is so designed as to satisfy the following conditions (3) and (4):

$$\Phi_2 + \Phi_3 < -0.55 \quad (3)$$

$$0.3 < -r_2/r_1 < 1 \quad (4)$$

wherein reference symbol $\Phi_2$ represents refractive power of an image side surface of the first lens component, reference symbol $\Phi_3$ designates refractive power of an object side surface of the second lens component, and reference symbols $r_1$ and $r_2$ denote radii of curvature on an object side surface and the image side surface respectively of the first lens component.

12. A television camera for endoscopes according to claim 1 wherein said imaging lens system consists of a lens component having positive refractive power and is so designed as to satisfy the following condition (5):

$$|r_b/r_A| < 1 \quad (5)$$

wherein reference symbols $r_A$ and $r_B$ represent radii of curvature on an extreme object side surface and an extreme image side surface of said lens component.

13. A television camera for endoscopes according to claims 10, 11 or 12 wherein a stop is arranged in front of said imaging lens system.

* * * * *